(12) United States Patent
Schuman et al.

(10) Patent No.: US 7,086,860 B2
(45) Date of Patent: Aug. 8, 2006

(54) IMPLANT PLACEMENT SYSTEM

(76) Inventors: Walter F. Schuman, 17 Alderte Rd., Peralta, NM (US) 87042; Gordan D. Blacklock, 3321 Columbia, NE. Albuquerque, NM (US) 87107

( * ) Notice: Subject to any disclaimer, the term of this patent is extended or adjusted under 35 U.S.C. 154(b) by 0 days.

(21) Appl. No.: 10/877,406

(22) Filed: Jun. 24, 2004

(65) Prior Publication Data

US 2004/0234922 A1    Nov. 25, 2004

Related U.S. Application Data

(63) Continuation-in-part of application No. 10/078,002, filed on Feb. 20, 2002, now Pat. No. 6,913,463.

(51) Int. Cl.
*A61C 3/02* (2006.01)

(52) U.S. Cl. .......................... 433/75; 433/76

(58) Field of Classification Search ............. 433/72, 433/74, 75, 76, 213, 214
See application file for complete search history.

(56) References Cited

U.S. PATENT DOCUMENTS

| | | | |
|---|---|---|---|
| 4,575,805 A | | 3/1986 | Moermann et al. |
| 4,738,619 A | | 4/1988 | Ross |
| 5,015,183 A | * | 5/1991 | Fenick ................. 433/76 |
| 5,133,660 A | * | 7/1992 | Fenick ................. 433/76 |
| 5,176,516 A | * | 1/1993 | Koizumi ............... 433/72 |
| 5,320,462 A | | 6/1994 | Johansson et al. |
| 5,320,529 A | * | 6/1994 | Pompa ................. 433/76 |
| 5,372,502 A | | 12/1994 | Massen et al. |
| 5,401,170 A | | 3/1995 | Nonomura |
| 5,556,278 A | * | 9/1996 | Meitner ................ 433/75 |
| 5,587,912 A | | 12/1996 | Andersson et al. |
| 5,613,852 A | * | 3/1997 | Bavitz ................. 433/173 |
| 5,718,579 A | * | 2/1998 | Kennedy ............... 433/75 |
| 5,725,376 A | | 3/1998 | Poirier |
| 5,769,636 A | * | 6/1998 | Di Sario .............. 433/213 |
| 5,823,778 A | | 10/1998 | Schmitt et al. |

(Continued)

FOREIGN PATENT DOCUMENTS

WO    WO 90/11046    * 10/1990

OTHER PUBLICATIONS

Basic Dental Implants, web page http://webarchive.org/web/2004/20042012014501/http://www.basicdentalimplants.com/dentists_ . . . © 2002,2003.*

(Continued)

*Primary Examiner*—Ralph A. Lewis
(74) *Attorney, Agent, or Firm*—Ray R. Regan

(57) ABSTRACT

The specification and drawing figures describe and show an implant placement system that includes one or more graphic representations of a proposed dental implant site, and a device for determining bone and soft tissue data at the proposed dental implant site ("site"). A model is formed of the site for portraying dental implant site data. A variety of tools are sued to determine the size and angulations of the dental implant. After cutting the model, additional tools are used for drawing a graphic on the model. A pin, formable material and an implant guide are provided to transfer the placement information to the site. A drill is use to form a channel for the implant device.

5 Claims, 18 Drawing Sheets

U.S. PATENT DOCUMENTS

| | | |
|---|---|---|
| 5,842,858 A | 12/1998 | Truppe |
| 5,851,115 A | 12/1998 | Carlsson et al. |
| 5,857,853 A | 1/1999 | van Nifterick et al. |
| 5,927,982 A | 7/1999 | Kruger |
| 6,224,373 B1 * | 5/2001 | Lee et al. .................. 433/172 |
| 6,261,098 B1 | 7/2001 | Persson |
| 6,532,299 B1 | 3/2003 | Sachdeva et al. |
| 6,814,575 B1 * | 11/2004 | Poirier ........................ 433/75 |
| 6,869,282 B1 * | 3/2005 | Carmichael et al. .......... 433/76 |

OTHER PUBLICATIONS

Pierre Boudrias DMD MSD; Evaluation of the osseous edentulous ridge; The Dental Chronicle of the Assc of Prosthodontists of Quebec;Jul. 2003;pp. 301-302; vol. 40; Quebec.

* cited by examiner

IMPLANT PLACEMENT SYSTEM

CROSS-REFERENCE TO RELATED APPLICATION

This application is a continuation-in-part of U.S. application, Ser. No. 10/078,002, now U.S. Pat. No. 6,913,463, entitled a Drilling Guide for Dental Implantation, filed Feb. 20, 2002, naming as the inventor one co-inventor named in this document.

FIELD OF TECHNOLOGY

The apparatus and methods disclosed in this document pertain generally to dental implantation. More particularly, the new and useful implant placement system disclosed and claimed in this document provides an inexpensive but accurate and reliable system for determining the introduction point for placement of an implant, and for accurately defining three-dimensional axes for an implant channel for emplacement of an implant in a jaw.

BACKGROUND

While a number of dental implant placements methods currently are advocated, most require expensive machines and tools aided by computer-assisted technologies to prepare a dental implant site and to insert a dental implant in the site. Limitations of prior approaches include at least the considerable expense for sophisticated equipment and personnel to perform dental implants. A need exists in the industry for a new, useful and improved dental implant placement system capable of allowing a doctor or technician to inexpensively but accurately insert a dental implant.

SUMMARY

The implant placement system includes apparatus to diagnose an implantation protocol, and a method for placing an implant at an implant site. Accordingly, the implant placement system is useful in (1) determining bone and soft tissue data using tools familiar to all dentists and technicians (collectively, in this document, "dental technician"); (2) preparing and using a plaster model of the dental implant site using materials and tools also familiar to dental technicians; (3) using the plaster model, in combination with a pin mountable within the plaster model to locate the point atop the implant site, and direction within the implant site, for drilling a channel; (4) also using the plaster model, in combination with implant silhouettes and similar tools to determine the angles at which the pin should be inserted into the model; (5) forming with a malleable, formable, and curable material a form that holds the pin and a drilling guide substantially stationary; and (6) physically transferring the form and drilling guide to a patient's implant site to locate the axes along which the channel should be formed using a tool such as a drill.

In general, the implant placement system includes use of one or more graphic representations of the proposed dental implant site and adjacent teeth and jaw area, made using conventional photograph radiographs, film or digital, available in most dental offices (collectively, "graphic representations"). The system also includes a device for determining bone and soft tissue data, including at least bone and soft tissue dimensions, at the proposed dental implant site. Further, a model of the proposed dental implant site for portraying dental implant site data is prepared by making a plaster model from an impression that has been formed of a material having properties like rubber. The plaster model is cut transversely, important data are recorded physically on transverse faces of the cut model, and a pin positioning tools are used for determining the introduction point. A form is made from a malleable and curable substance that holds the pin assembly substantially stationary and, following the curing stage, can be transferred to a patient's proposed implant site to accurately and inexpensively mark the introduction point and the angles for drilling the channel into which the implant guide will be inserted.

It will become apparent to one skilled in the art that the claimed subject matter as a whole, including the structure of the apparatus, and the cooperation of the elements of the apparatus, combine to result in a number of unexpected advantages and utilities. The structure and co-operation of structure of the implant placement system will become apparent to those skilled in the art when read in conjunction with the accompanying following description, drawing figures, and appended claims.

The foregoing has outlined broadly the more important features of the invention to better understand the detailed description that follows, and to better understand the contributions to the art. The implant placement system is not limited in application to the details of construction, and to the arrangements of the components, provided in the following description or drawing figures, but is capable of other embodiments, and of being practiced and carried out in various ways. The phraseology and terminology employed in this disclosure are for purpose of description, and therefore should not be regarded as limiting. As those skilled in the art will appreciate, the conception on which this disclosure is based readily may be used as a basis for designing other structures, methods, and systems. The claims, therefore, include equivalent constructions. Further, the abstract associated with this disclosure is intended neither to define the implant placement system, which is measured by the claims, nor intended to limit the scope of the claims. The novel features of the implant placement system are best understood from the accompanying drawing, considered in connection with the accompanying description of the drawing, in which similar reference characters refer to similar parts, and in which:

DETAILED DESCRIPTION

As shown in FIGS. 1–38, a implant placement system is provided that in its broadest context includes apparatus to conduct a six-step procedure for placing a dental implant in an implant site: (1) determining bone and soft tissue data using tools familiar to all dentists and technicians (collectively, in this document, "dental technician"); (2) preparing a plaster model of the dental implant site using materials and tools also familiar to dental technicians; (3) using the plaster model, in combination with a silhouette and similar tools to locate the point on the model where the dental technician should drill a channel for inserting an implant pin; (4) placing the pin into the channel; (5) forming with a malleable and curable substance a form that holds the pin assembly substantially stationary; and (6) physically transferring the form to a patient's implant site to locate the axes on which the drill should prepare the implant site.

Figure 29:
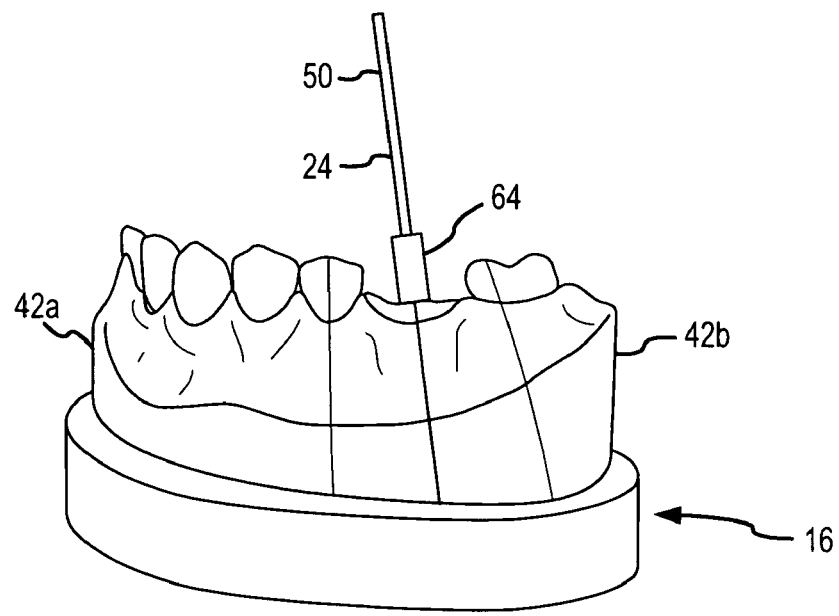
FIG. 29 is a side perspective view showing a slidably engageable implant guide inserted over the pin.
Figure 30:
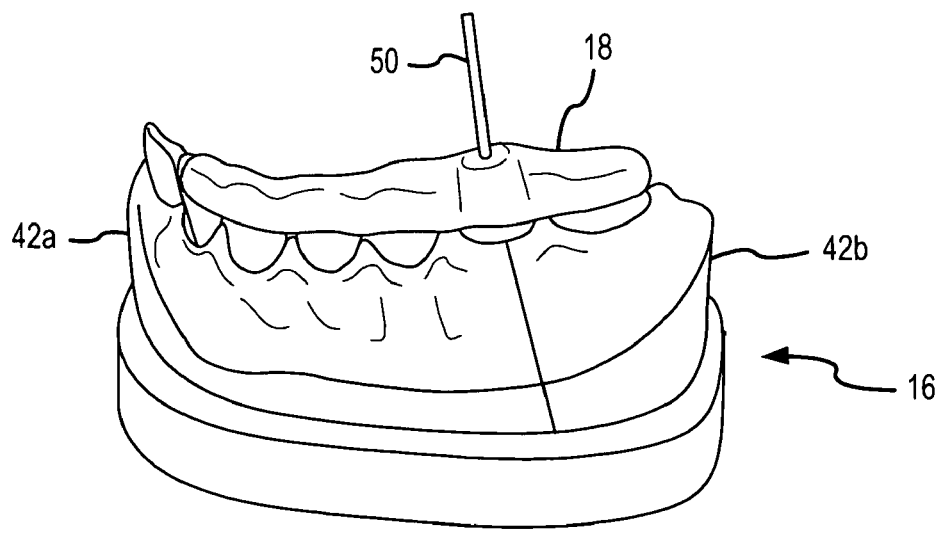
FIG. 30 is a side perspective view of the model with a moldable material formed over the reassembled model.
Figure 31:
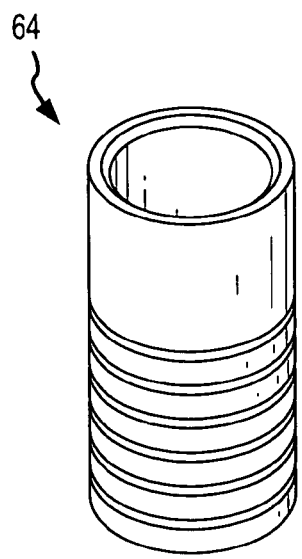
FIGS. 31–34 are perspective views showing one component of exemplary implant guide.
Figure 32:
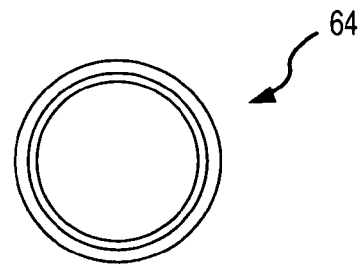
Figure 33:
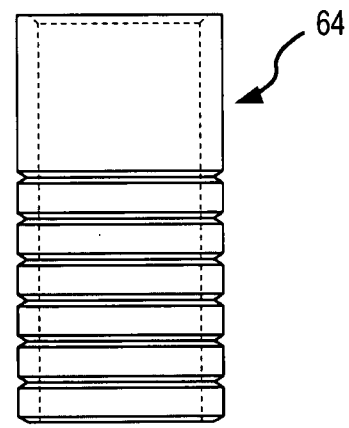
Figure 34:
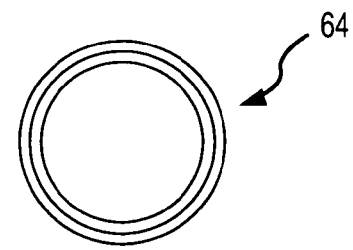
Figure 35:
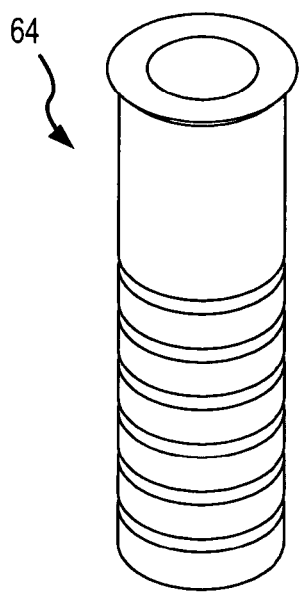
FIGS. 35–38 are another exemplary presentation of the implant guide.
Figure 36:
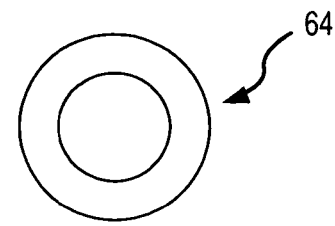
Figure 37:
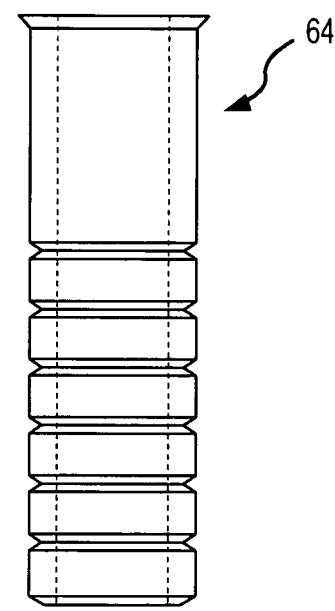
Figure 38:
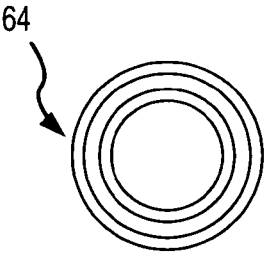

More specifically, as shown in FIGS. 1–38, an implant placement system 10 is provided that in its broadest context includes one or more graphic representations 12 of a proposed implant site 14. One or more graphic representations 12 may be selected from a group of graphic representations consisting of photographs, x-ray photographs, panographs, and digital graphic representations. In addition, implant placement system 10 includes a model 16. Model 16 is created to portray the actual proposed implant site 14. Model 16 is created for depicting data in connection with proposed dental implant site 14. Also, included in implant placement system 10 is a moldable form 18 as shown in FIG. 30. As shown by cross-reference between FIGS. 5–6, and FIGS. 9–12, model 16 is formed of plaster. Model 16 formed of plaster is further formed from an impression of the dental arch 20 at proposed implant site 14 as shown by cross-reference between FIGS. 3 and 4. As will be evident to one skilled in the art, model 16 is a plaster model 16 that is cured from a pour-up from an impression of proposed dental implant site 14. Moldable form 18 installable on model 16 is useful for transferring desired drilling axis 22 from model 16 to proposed implant site 14 of a patient.

Figure 25:
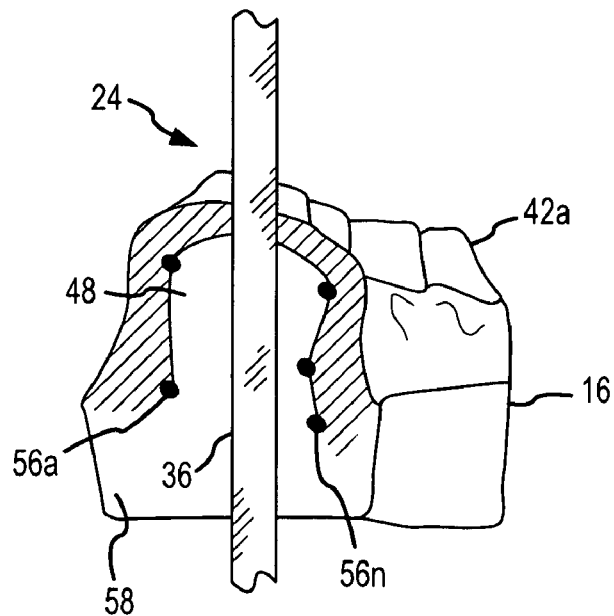
FIG. 25 is a perspective end view showing desired drill location.
Figure 26:
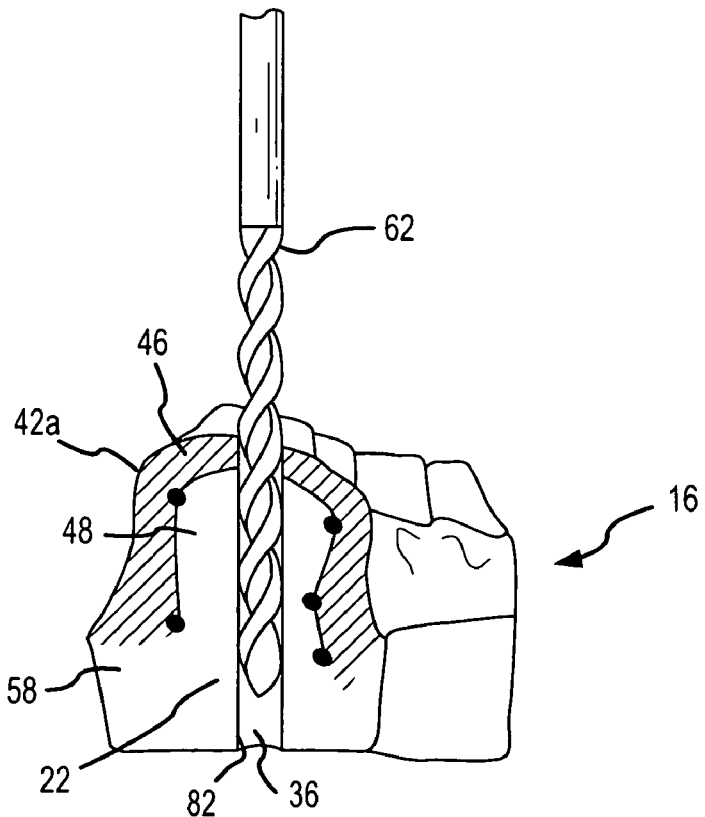
FIG. 26 is a perspective end view showing insertion of a drill bit in the model.
Figure 27:
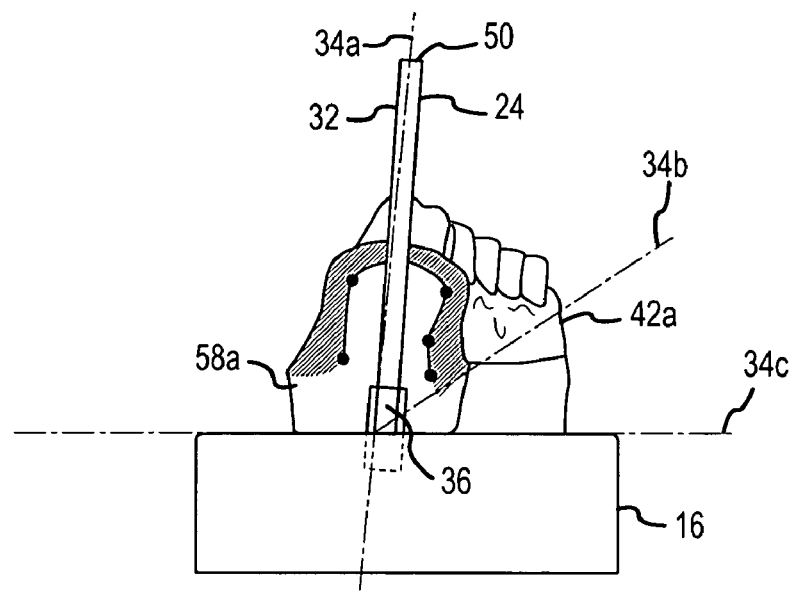
FIG. 27 is a perspective end view showing insertion of a pin.
Figure 28:
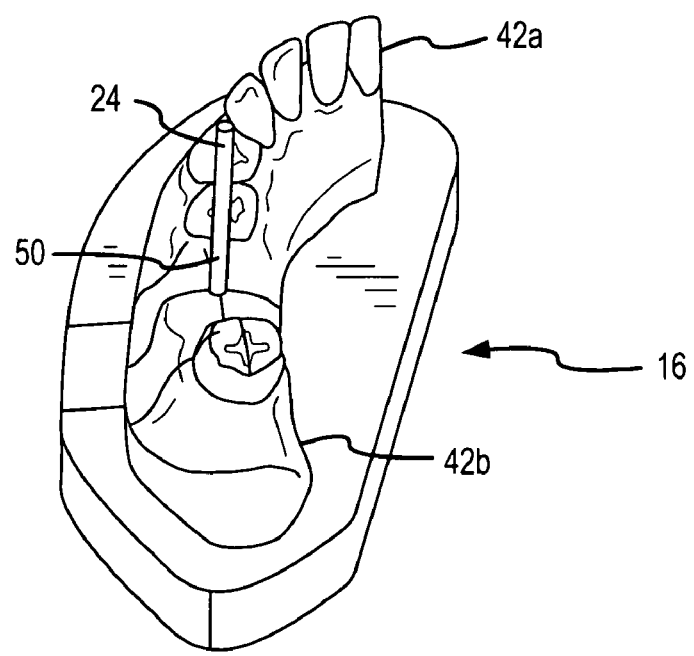
FIG. 28 is a top perspective view showing reassembly of the model with the pin inserted.

In addition, implant placement system 10 includes one or more channel positioning tools 24. As best shown by cross-reference among FIGS. 7–8, 13–22, and 25–38, channel positioning tools 24 include a device 26 for determining bone and soft tissue data. Device 26 for determining bone and soft tissue data includes in one embodiment a needle 28. Device 26 for determining bone and soft tissue data, in another embodiment, includes a needle and a stop 30 slidably engageable with needle 28. As further shown in FIGS. 1–38, device 26 for determining bone and soft tissue data is a tissue-penetrating needle 28'. In another embodiment, device 26 for determining bone and soft tissue data includes a stop 30' that is slidably engageable with needle 28'. In operation, stop 30 is useful in determining depth of bone and soft tissue. One or more channel positioning tools 24, as shown in FIGS. 25–27, provides means 32 for defining three axes 34a–c of implant channel 36 as shown in FIG. 27.

Figure 2:
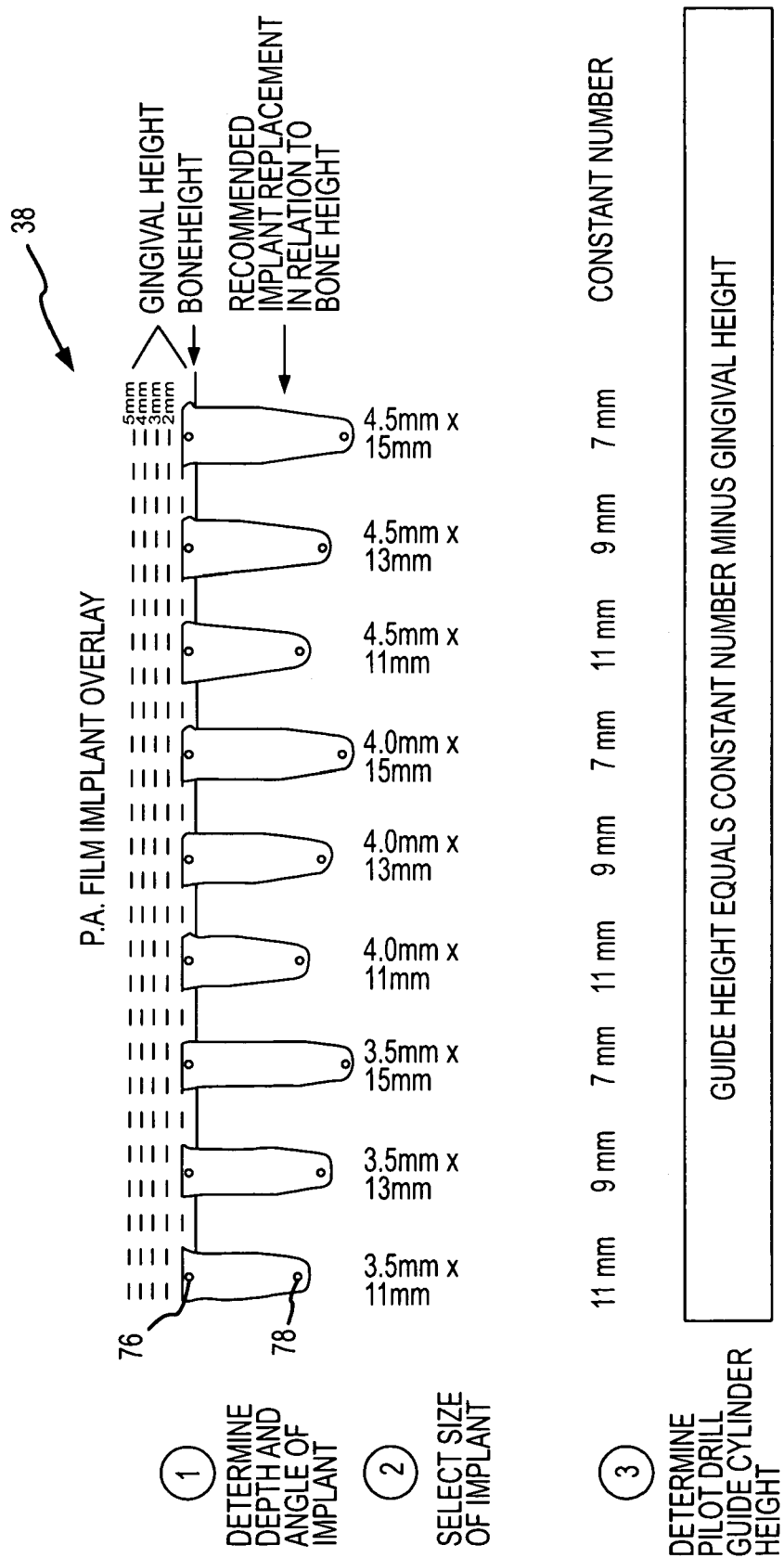
FIG. 2 is a diagrammatic representation of a film implant overlay.

In the embodiment illustrated in FIG. 2, an implant placement system 10 includes a silhouette 38. Silhouette 38 is used by a technician during operation of implant placement system 10 for determining size and angulation of a dental implant 40. In addition, one or more channel positioning tools 24 of implant placement system 10 includes a cutter (not shown) for making a tomographic transverse cut of model 16 into at least two segments 42a,b as perhaps best shown in FIGS. 11–12 and 19–27. The cutter (not shown) may be selected from a group of cutters consisting of straight saws, rotating circular saws, electric and electrical cutters, and heat-activated cutters. Also included is a marker (not shown) for drawing a graphic rendition 44a,b of the covering tissue 46 and the underlying bone 48. The marker (not shown) is selected from a group of markers consisting of pens, pencils, soft-tipped fine indelible markers, brushes, and electronic and electrical markers. Graphic rendition 44a of tissue 46, and graphic rendition 44b of bone 48, are perhaps best shown by cross-reference between FIGS. 21–22.

Figure 3:
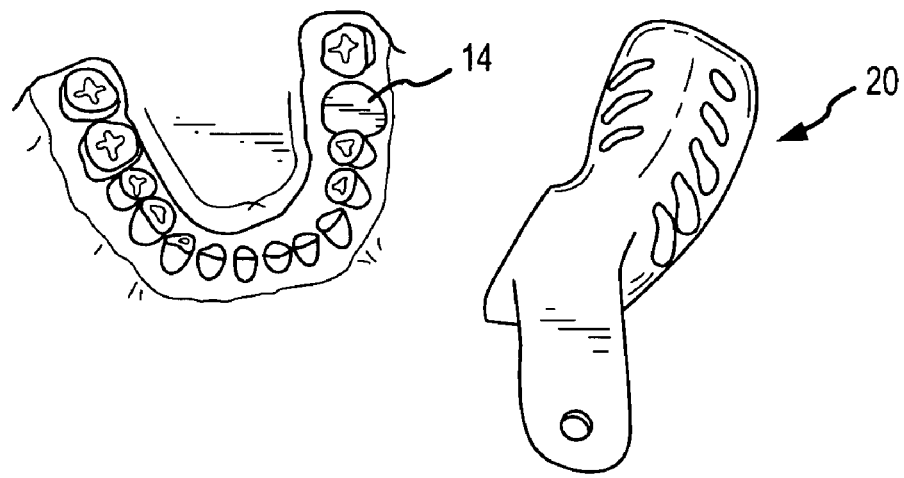
FIG. 3 is a perspective view of an actual dental implant site and a tool for forming an impression.
Figure 4:
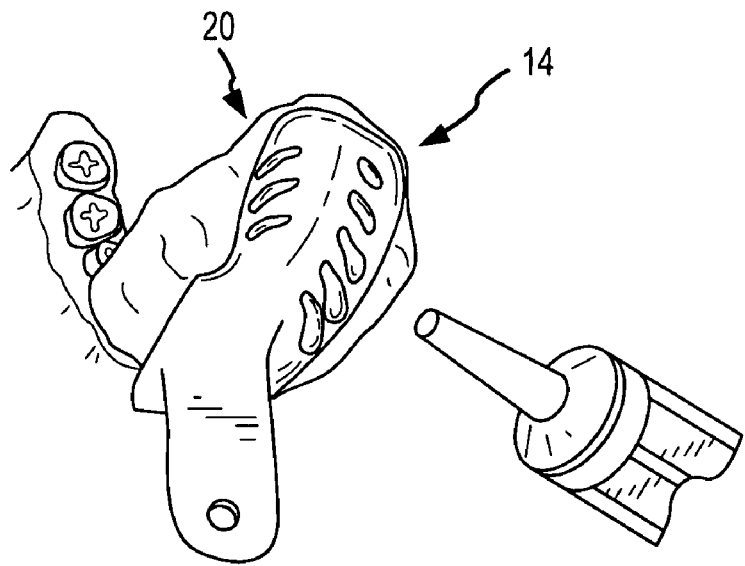
FIG. 4 is a perspective view showing the formation of an impression.
Figure 5:
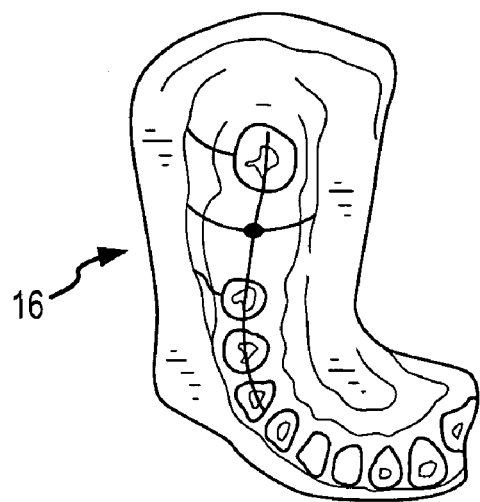
FIG. 5 is a perspective view of the model showing markings.
Figure 6:
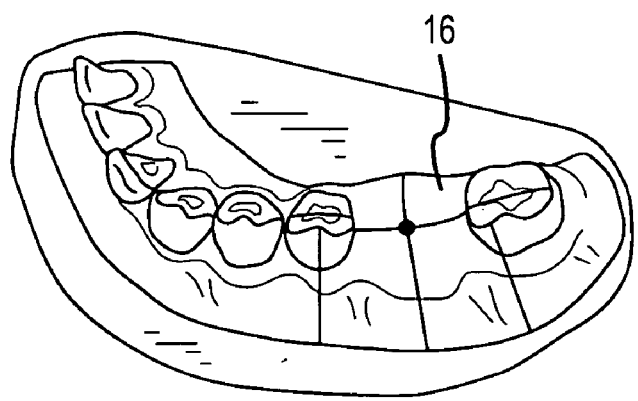
FIG. 6 is another perspective view of the model with markings on the implant site.
Figure 7:
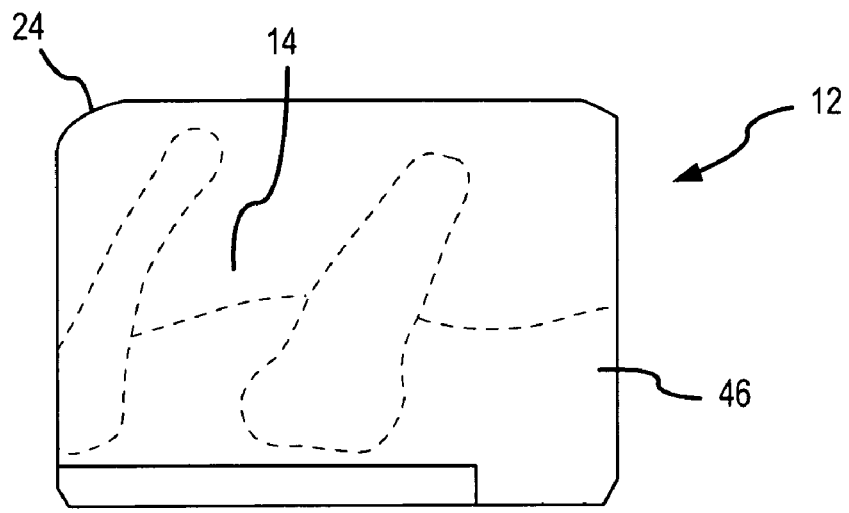
FIG. 7 is a graphical representation of the implant site.
Figure 8:
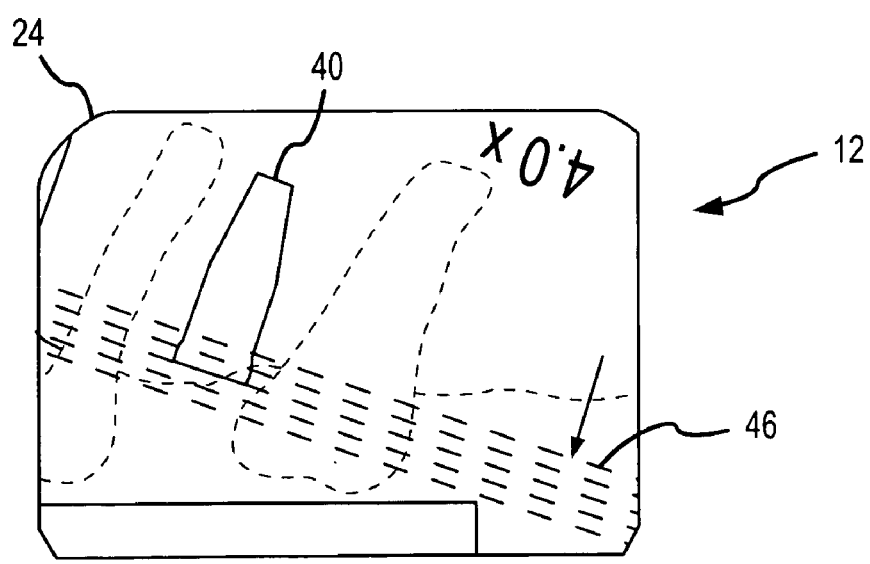
FIG. 8 is a graphical representation of the implant site and proposed implant.
Figure 9:
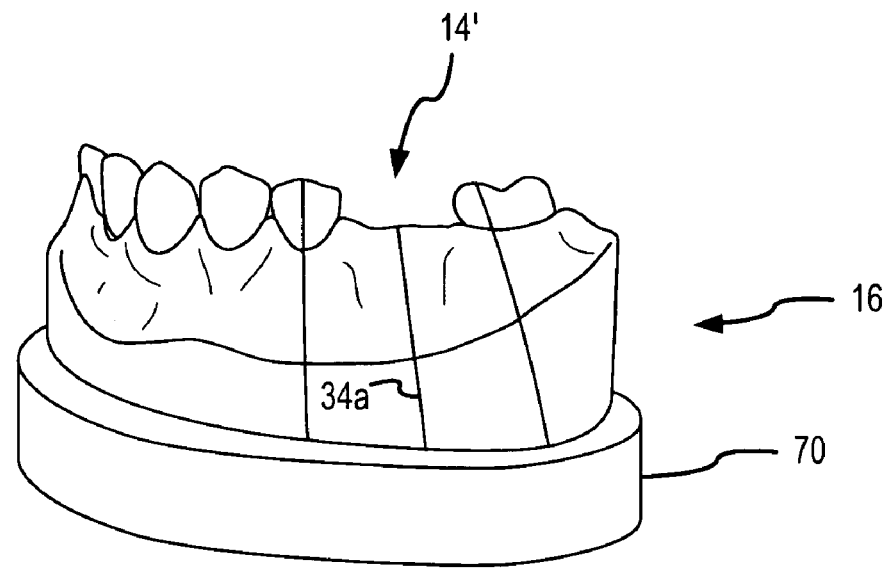
FIG. 9 is a front view of the model.
Figure 10:
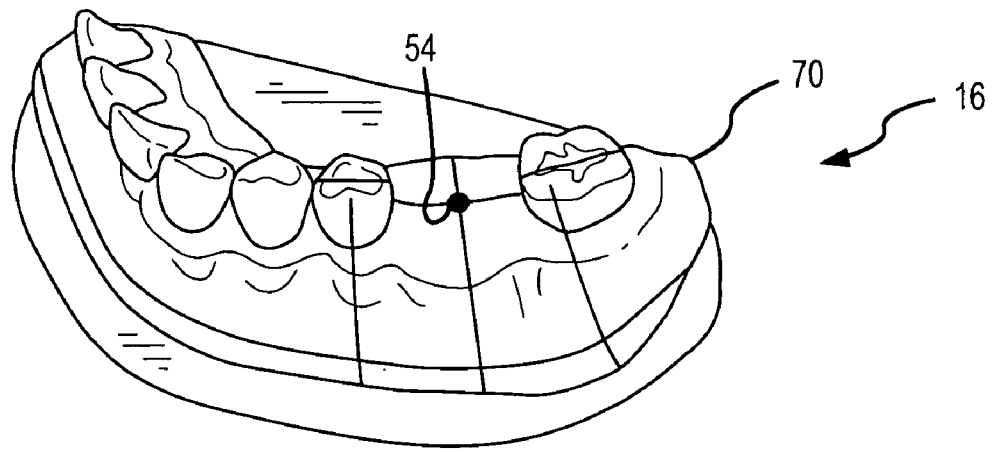
FIG. 10 is a top view of the model showing the implant site.
Figure 11:
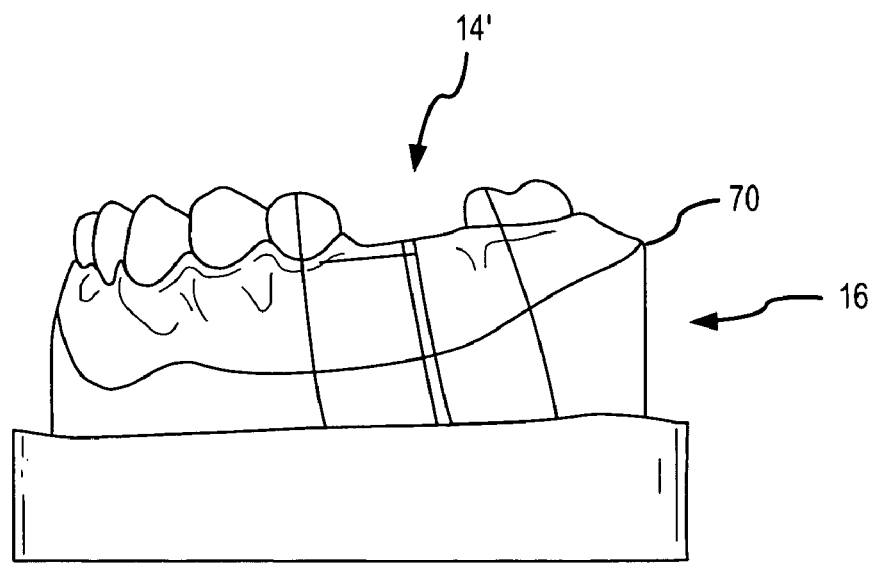
FIG. 11 is a front view of a proposed cutting of the model.
Figure 12:
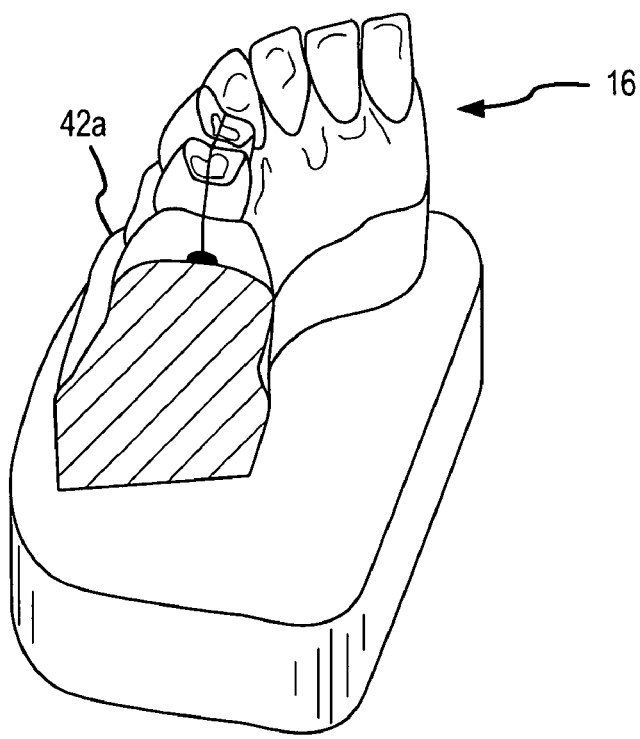
FIG. 12 shows a cut-away of one segment of the model.
Figure 13:
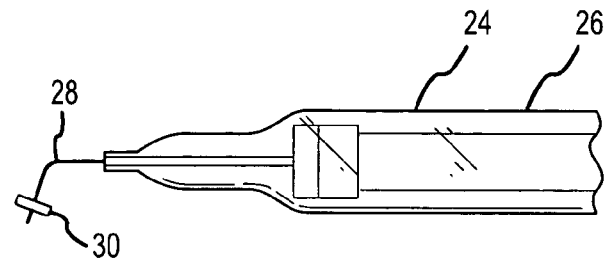
FIG. 13 is a side view of a tool for determining depth of tissue and bone.
Figure 14:
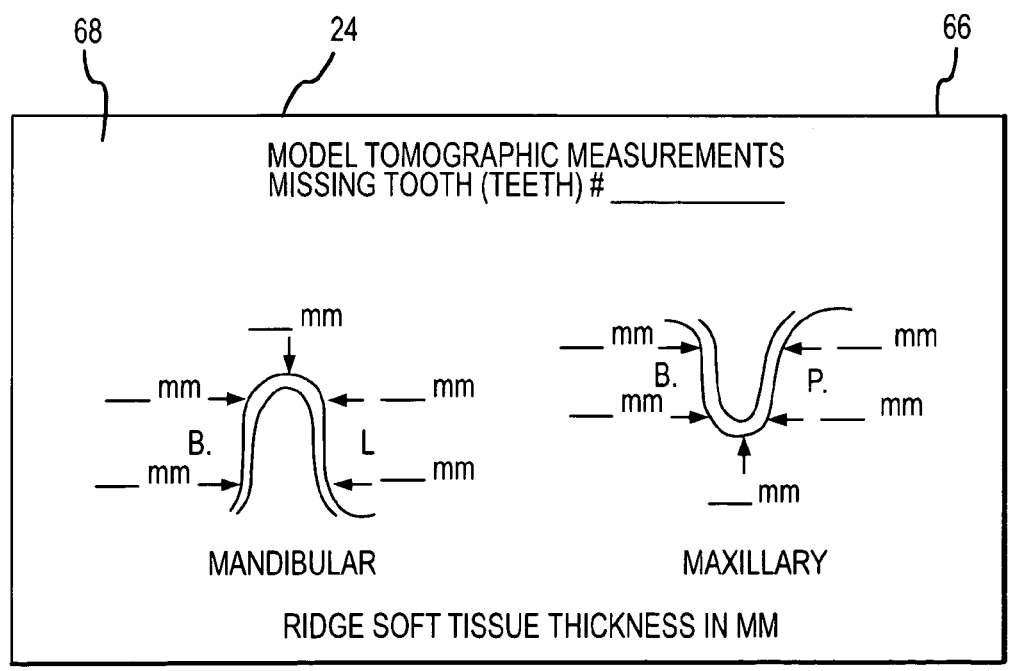
FIG. 14 is a diagrammatic presentation of a measurements label.
Figure 15:
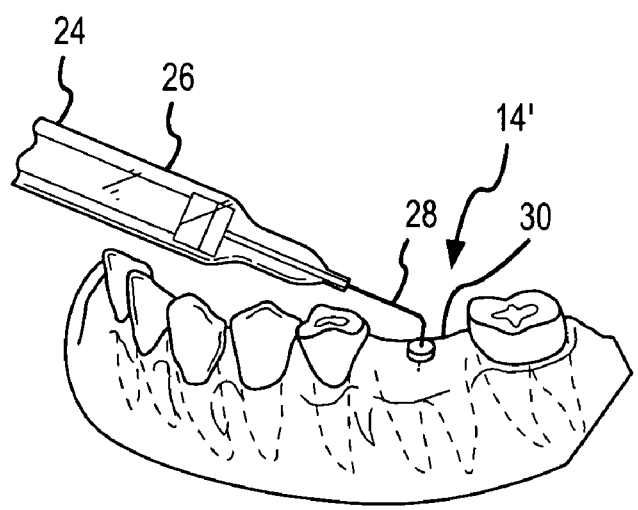
FIG. 15 is a perspective view showing use of the measurements-determining tool.
Figure 16:
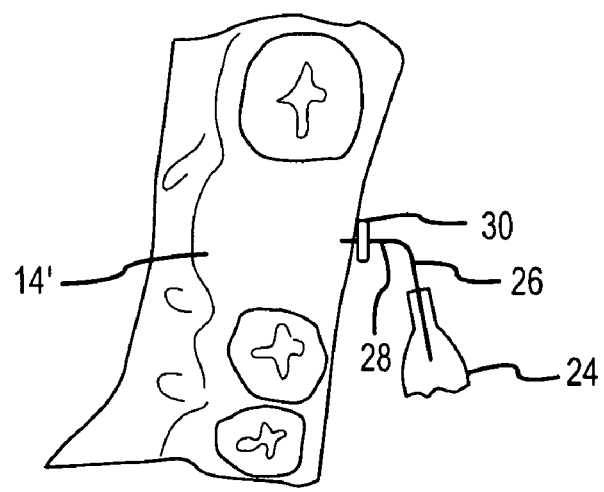
FIG. 16 is a perspective view of use of the measurements-determining tool for determining tissue depth at a proposed implant site.
Figure 17:
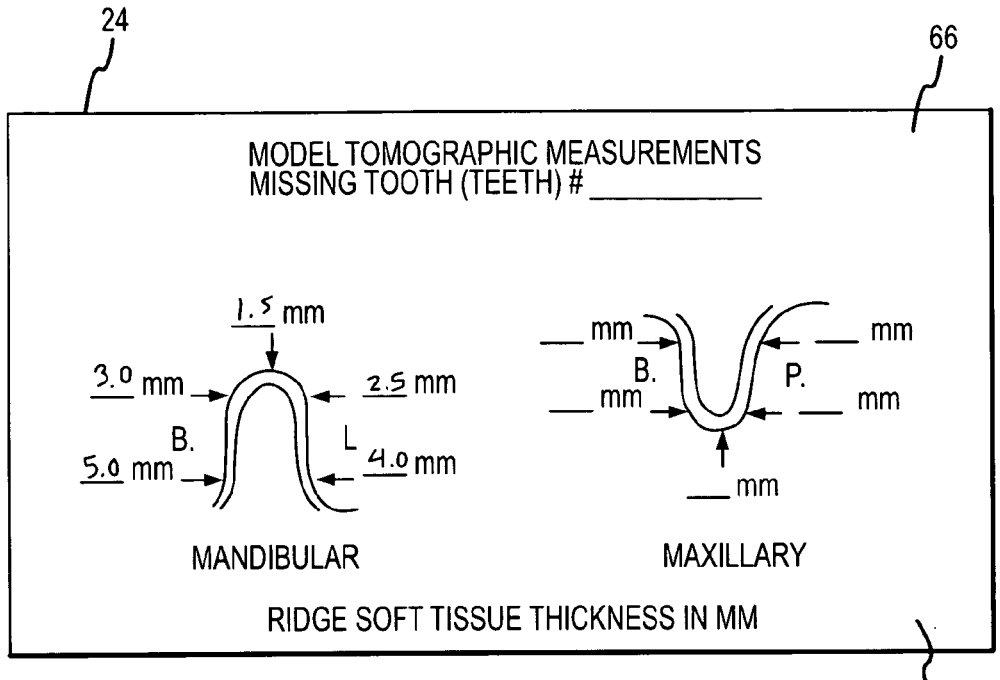
FIG. 17 is a diagrammatic representation of use of the label shown in FIG. 14.
Figure 18:
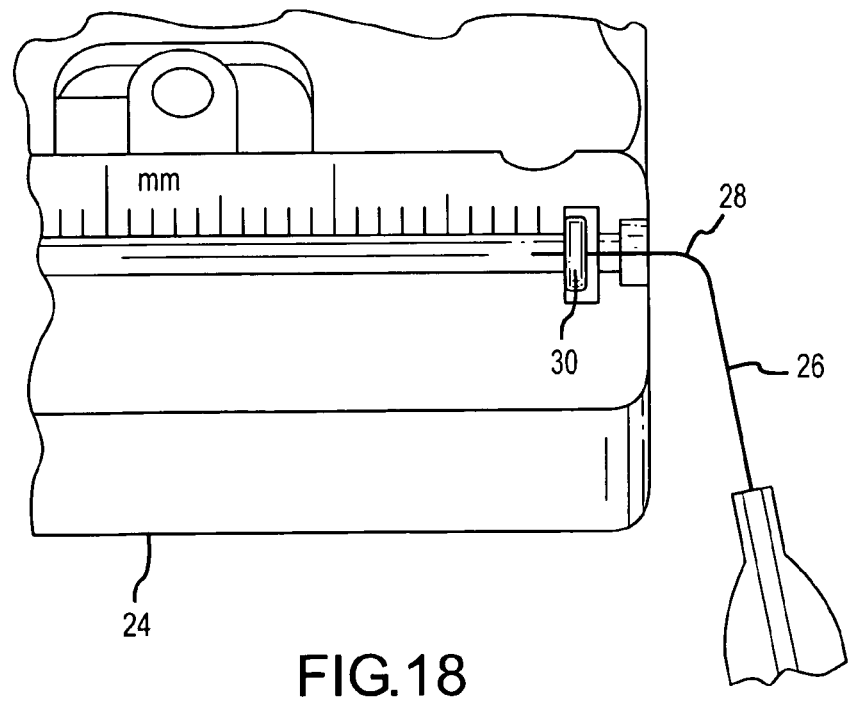
FIG. 18 is a cut-away view showing a measurement means for ascertaining dimensions.
Figure 19:
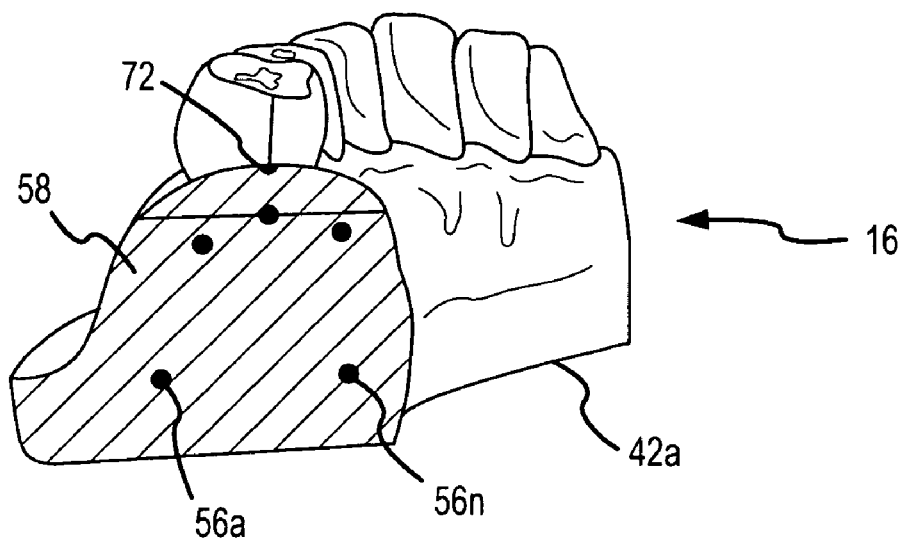
FIG. 19 is an end perspective view of a cut-away segment of the model.
Figure 20:
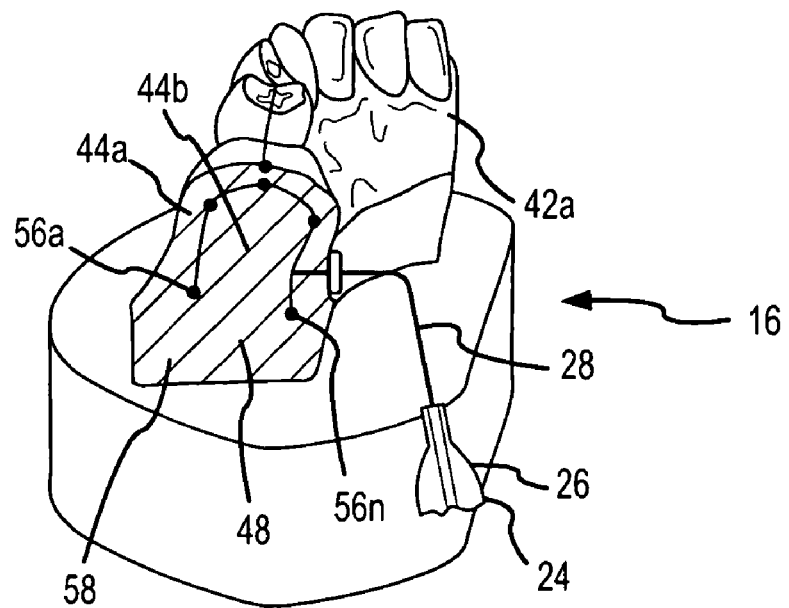
FIG. 20 is an end perspective view of the cut-away segment shown in FIG. 19 showing use of the dimension-determining tool.
Figure 21:
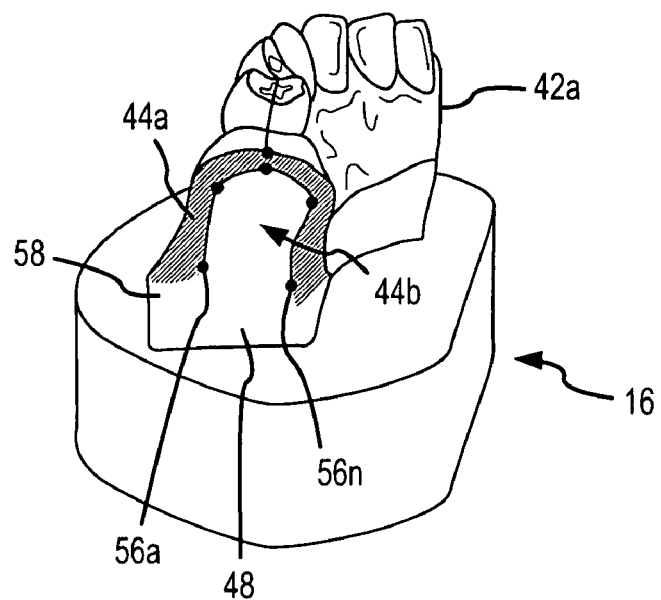
FIG. 21 is an end view of the cut-away segment of the model showing various dimensions marked on the model segment.
Figure 22:
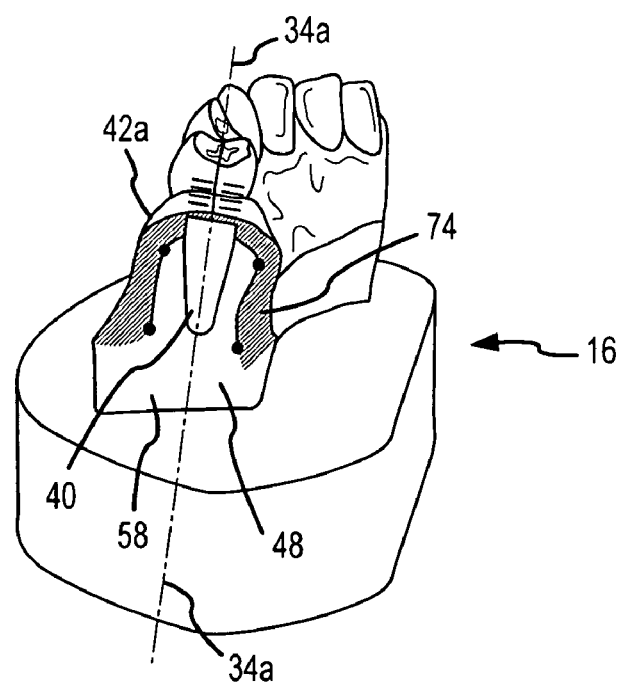
FIG. 22 is perspective end view of the segment shown in FIG. 21 with a depth and angle determination.
Figure 23:
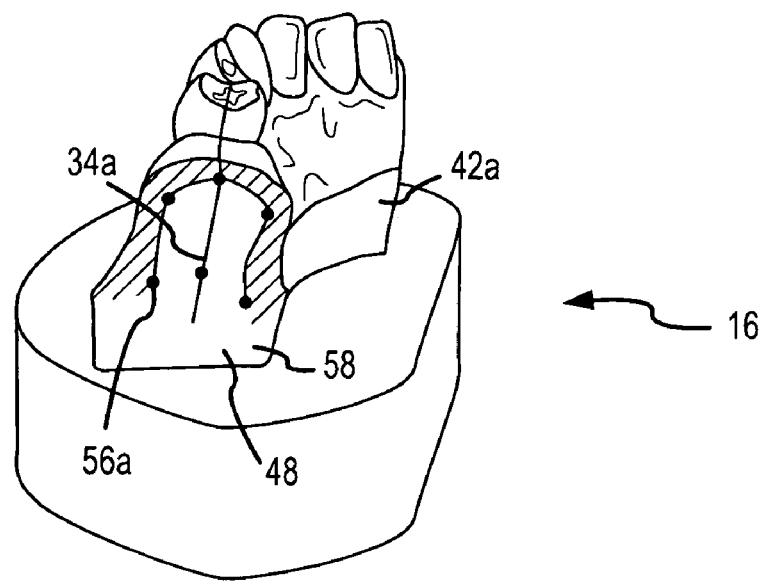
FIG. 23 is the perspective end view shown in FIG. 21 with all markings indicated.
Figure 24:
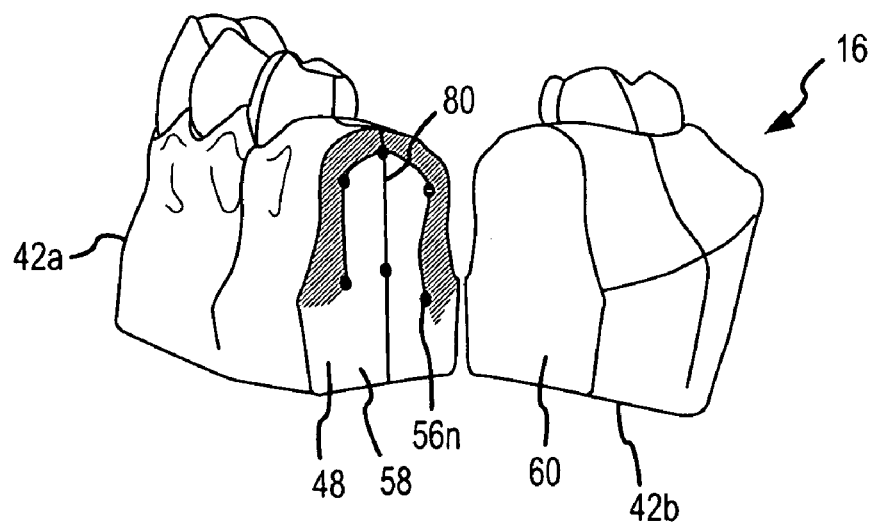
FIG. 24 shows the relationship between the marked-up end view and the second segment of the cut-away model.

As indicated, implant placement system 10 includes in one embodiment impression 20 as shown in FIG. 3. Impression 20 is made of a malleable curable substance. As best shown in FIGS. 3–4, impression 20 is created by packing the malleable curable substance on implant site 14 of a patient, as perhaps best shown in FIG. 4. Cured moldable form 18 is removable from model 16 and transferable to the actual implant site 14. In operation, during formation of moldable form 18, a pin 50, as perhaps best shown by cross-reference between FIGS. 27–30, is inserted into a channel 36 formed in model 16, usually in a segment 42a, before reassembly of segments 42a and 42b into a single or reassembled model 16, as perhaps best shown in FIG. 30. In connection with channel 36, implant placement system 10 includes means 54 for locating channel 52 on model 16. Means 54 for locating channel 52 includes use of silhouette 38 as shown in FIG. 2. Graphic renditions 44a,b of tissue 46 and of bone 48 are marked on segment 42a as shown by cross-reference between FIGS. 19–24. As perhaps best shown in FIGS. 19–20, a series of dots 56a–n are located on a first surface 58 of segment 42a to correspond to the tissue 46 and bone 48 data obtained from use of device for determining bone and soft tissue data 26 such as needle 28 and stop 30. To the extent that subscripts to numerical designations include the lower case letter "n," as in "a–n," the letter "n" is intended to express a large number of repetitions of the element designated by that numerical reference and subscript. Using a marker (not shown), series of dots 56a–n may be connected as shown in FIGS. 20–22. Further, using silhouette 38 as shown in FIG. 2, the location and at least one axis 34a of the three desirable axes 34, as shown in FIGS. 9, 26, and 27, may be superimposed on the first surface 58 of segment 42a. As further shown in FIG. 24, segment 42b having second surface 60 is rejoined with first surface 58 of segment 42a of model 16. A drill bit 62, of the kind well known to those skilled in the art, as shown in FIG. 26, may be used to form first channel 36 in model 16. Pin 50 is inserted into channel 36, as perhaps best shown by cross-reference between FIGS. 27–30. A dental implant guide 64 is removably insertable over pin 50, as shown in FIG. 29. Moldable form 18 is packed around reassembled segments 42a,b of model 16, pin 50, and dental implant guide 64, as shown best in FIG. 30.

Implant placement system 10 also includes means 66 for recording site data obtained from application of the device 26 for determining bone and soft tissue data. Means 66 for recording implant site data, in one embodiment, includes the label 68 shown in FIG. 14, and also shown in FIG. 17. As will be evident to one skilled in the art, label 68 is merely one example, although exemplary, of means 66 for recording implant site data for reference and use by a technician.

The implant placement system shown in drawing FIGS. 1–38 includes a number of embodiments none of which is intended to be exclusive, but merely illustrative of the disclosed but non-exclusive embodiments. Claim elements and steps have been numbered solely as an aid in readability and understanding. The numbering is not intended to, and should not be considered as intending to, indicate the ordering of elements and steps in the claims. Means-plus-function clauses in the claims are intended to cover the structures described as performing the recited function, which include not only structural equivalents, but also equivalent structures. Thus, although a nail and screw may not be structural equivalents, in the environment of the subject matter of this document a nail and a screw may be equivalent structures.

OPERATION

In operation, as shown by cross-reference between FIGS. 1–38, implant placement system 10 is used by a technician to properly place an implant 40 at an implant site 14. The technician obtains one or more graphic representations 12 of a proposed implant site 14. Bone and tissue data are collected in connection with the actual implant site 14. Bone and tissue data are collected using, in combination, model 16, channel positioning tools 24, which include a device 26 for determining bone and soft tissue data, silhouette 38, pin 50, means 54 for locating channel 36, drill bit 62, dental implant guide 64, and means 66 for recording implant site data on model 16, specifically on segments 42a,b of model 16. Moldable form 18, and dental implant guide 64 collectively in place, are transferred to implant site 14, thus identifying for the technician the three axes along which channel 36 may be formed in implant site 14 for insertion of dental implant 40.

Figure 1:
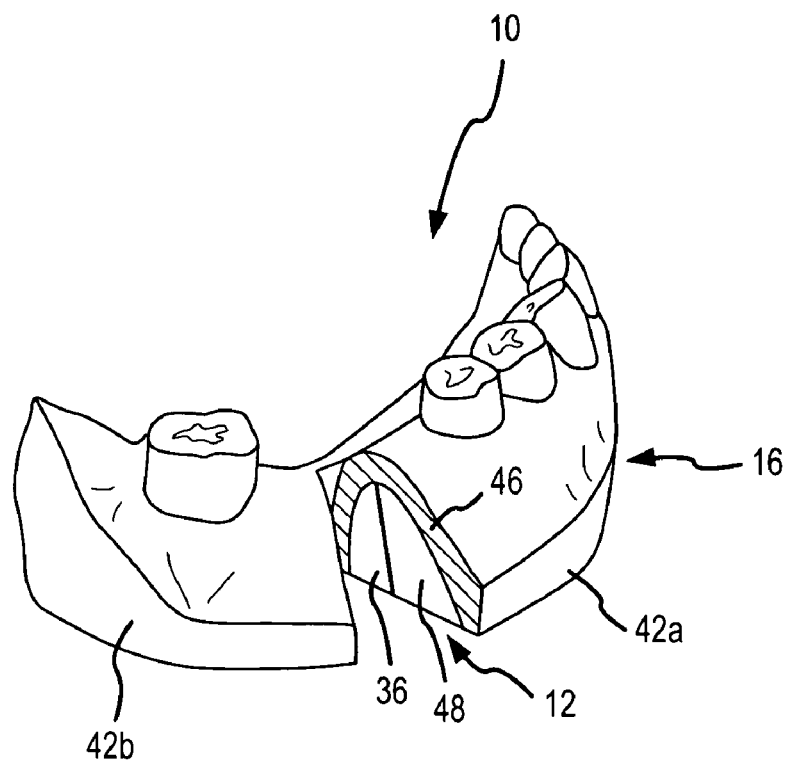
FIG. 1 of the drawing is a perspective view of a model of a dental implant site.

After an impression 20 is made, plaster model 16 may be cast from impression 20. Plaster cast 70 is cured to form model 16 as best shown in FIG. 1 As also shown in FIG. 1, plaster cast 70 may be trimmed before use of the cast as model 16.

Further, a preliminary mark 72, as best shown in FIGS. 19–22, may be placed on plaster cast 70 at a proposed functional and aesthetic location for dental implant 40. Using silhouette 38, the preferred lateral direction and size of dental implant 40 may be selected as shown in FIG. 22. In addition, one or more adjacent root angulation lines may be scribed on plaster cast 70 as indicated by FIG. 9. Using a cutter (not shown), plaster cast 70 is cut at substantially right angles to the longitudinal axis through the preliminary mark 72 at appropriate distances and angulations of adjacent teeth to form segments 42a,b. Cutting plaster cast 70 into segments 42a,b exposes both first surface 58 of segment 42a and second surface 60 of segment 42b. Exposing first surface 58 and second surface 60 allows a technician to scribe series of dots 56a–n on at least segment 42a, thus locating and showing on first surface 58 of segment 42a the collected soft tissue and hard tissue data. Placing silhouette 38 against the graphic 74 thus scribed on first surface 58 of segment 42a determines the preferred transverse direction of dental implant 40 at actual implant site 14, as well as the sizing of dental implant 40, as shown by cross-reference between FIGS. 19–22. In addition, additional dots 56a–n, as best shown by cross-reference to FIGS. 10–22, through holes formed in silhouette 38 may be used to locate the center top location 76 and the center apex location 78. The technician may draw a directional line 80 between series of dots 56a–n, including center apex location 78 and center top location 76, to disclose the optimal location of dental implant 40 at and within the proposed dental implant site 14. The technician also may form a groove 82 on first surface 58 of segment 42a coincident with directional line 80 that is dimensionally consistent with the sizing of dental implant 40 to identify the proper position and placement of dental implant 40 along the x-, y-, and z-axes within dental implant site 14.

What is claimed is:

1. In a model tomographic dental implant placement system, a method for positioning a dental implant comprising the steps of:

obtaining one or more graphic representations of a proposed implant site;

collecting bone and tissue data;

forming a model of the proposed dental implant site for depicting dental implant site data;

recording the bone and tissue data on the model, wherein the recording step includes the substeps of:

placing a preliminary mark on the plaster-like cast at a proposed functional and aesthetic location for the implant;

using a film implant silhouette to determine the preferred lateral direction and size of the dental implant;

drawing one or more adjacent root angulations lines on the plaster cast;

cutting the plaster-like cast substantially at right angles to the longitudinal axis through the preliminary mark at the appropriate distance and angulations of adjacent teeth and providing a leading segment and trailing segment of the plaster cast;

exposing by the cutting substep an inner planar surface on both the leading segment and the trailing segment;

drawing a graphic on at least one inner planar surface showing soft tissue and hard tissue data;

placing the film implant silhouette against the graphic to determine the preferred axial direction of the dental implant at the proposed implant site and sizing of the dental implant;

marking dots on the graphic through holes on the film implant silhouette the center top and center apex locations;

drawing a directional line between the dots to disclose the optimal location of the dental implant at the proposed dental implant site;

forming a groove on the planar surface coincident with the directional line dimensionally consistent with the sizing of the dental implant to identify the proper position of the dental implant in the x-, y-, and z-axes within the dental implant site;

selecting a plurality of pin positioning tools for locating an insert channel at the proposed implant site;

locating a pin in the model consistent with the bone and tissue data; and shaping a form to transfer the pin axes to the implant site.

2. In a model tomographic dental implant placement system, a method for positioning a dental implant as recited in claim 1, wherein the one or more graphic representation radiographs obtaining step includes the substep of disclosing teeth adjacent the proposed implant site.

3. In a model tomographic dental implant placement system, a method for positioning a dental implant as recited in claim 2, wherein the data-collecting step includes the substeps of:

choosing a device for measuring soft tissue depth adjacent the implant site;

obtaining a plurality of bone soundings to determine soft tissue and hard tissue data from which to determine the preferred axial direction of the dental implant; and recording the plurality of bone soundings.

4. In a model tomographic dental implant system, a method for positioning a dental implant as recited in claim 1, wherein the model forming step includes the substeps of:

taking an impression of the dental implant site;

casting the plaster-like material into the impression;

curing the plaster-like cast;

trimming the plaster-like cast; and forming a plaster die pin model with pin holding base.

5. In a model tomographic dental implant system, a method for positioning a dental implant as recited in claim 1 further comprising the substeps of:

selecting means for locating a channel on the model;

forming the channel;

inserting a guide pin in the channel;

choosing a dental implant guide removably insertable over the guide pin;

using a formable and curable material to secure the dental implant guide and capture the imprint of the surrounding data;

removing the cured formable and curable material and dental implant guide to an actual dental implant site; and placing the cured formable and curable material and dental implant guide in the implant site to guide the direction and depth of a bone drill at the patient's dental implant site.

* * * * *